United States Patent [19]
Brown et al.

[11] Patent Number: 5,149,622
[45] Date of Patent: Sep. 22, 1992

[54] SOLID PHASE ANALYTICAL DEVICE AND METHOD FOR USING SAME

[75] Inventors: William E. Brown, Grayslake; John M. Clemens; Sharon M. Devereaux, both of Gurnee; John G. Hofler, Ingleside; Kevin M. Knigge, Wheeling; Sarah E. Safford, Libertyville, all of Ill.

[73] Assignee: Abbott Laboratories, North Chicago, Ill.

[21] Appl. No.: 528,277

[22] Filed: May 21, 1990

Related U.S. Application Data

[63] Continuation of Ser. No. 831,013, Feb. 18, 1986, abandoned, which is a continuation-in-part of Ser. No. 784,416, Oct. 4, 1985, abandoned.

[51] Int. Cl.⁵ ............... C12Q 1/70; C12Q 1/14; G01N 21/00
[52] U.S. Cl. .................. 435/5; 435/7.34; 435/7.92; 435/36; 435/970; 435/971; 436/518; 436/527; 436/528; 436/531; 436/535; 436/530; 422/56; 422/58; 422/60; 422/61
[58] Field of Search ............ 435/7.1, 34, 36, 288, 435/5, 6, 805, 810, 7.92, 734, 970, 971; 436/807-809, 527, 528, 530, 531, 535, 518; 422/55-61

[56] References Cited

U.S. PATENT DOCUMENTS

| | | | |
|---|---|---|---|
| 3,260,413 | 7/1966 | Natelson | 436/44 X |
| 3,843,324 | 9/1974 | Edelman et al. | 436/529 X |
| 3,888,629 | 6/1975 | Bagshawe | |
| 3,951,748 | 4/1976 | Devlin | |
| 4,059,407 | 11/1977 | Hochstrasser | 23/253 |
| 4,099,886 | 7/1978 | Oliveira | 422/56 X |
| 4,160,008 | 7/1979 | Fenocketti et al. | 422/56 |
| 4,219,335 | 8/1980 | Ebersole | 436/808 X |
| 4,246,339 | 1/1981 | Cole et al. | 435/7 |
| 4,254,083 | 3/1981 | Columbus | 422/55 |
| 4,256,693 | 3/1981 | Kondo et al. | 435/805 X |
| 4,280,816 | 7/1981 | Elahi | 435/810 X |

(List continued on next page.)

FOREIGN PATENT DOCUMENTS

| | | |
|---|---|---|
| 0063810 | 11/1982 | European Pat. Off. |
| 0119622 | 9/1984 | European Pat. Off. |
| 0131934 | 1/1985 | European Pat. Off. |
| 0141647 | 5/1985 | European Pat. Off. |
| 0171150 | 2/1986 | European Pat. Off. |
| 0173375 | 3/1986 | European Pat. Off. |
| 0177352 | 4/1986 | European Pat. Off. |
| 0200381 | 11/1986 | European Pat. Off. |
| 0249418 | 12/1987 | European Pat. Off. |
| 8403151 | 8/1984 | World Int. Prop. O. |
| 8500870 | 12/1985 | World Int. Prop. O. |
| 0001603 | 12/1986 | World Int. Prop. O. |

OTHER PUBLICATIONS

Clinical Lab Products, Jun. 1985, pp. 27-28.
Valkirs et al., Clinical Chemistry, vol. 31, No. 9, 1985, pp. 1427-1431.
Product Brochure for Abbott Test Pack, Abbott Laboratories, North Chicago, Ill., Aug. 1986.

*Primary Examiner*—Esther L. Kepplinger
*Assistant Examiner*—Carol A. Spiegel
*Attorney, Agent, or Firm*—Lawrence S. Pope; Thomas D. Brainard

[57] ABSTRACT

A novel material and device useful in solid-phase binding assays to determine the presence or amount of an analyte in a test sample, particularly antigens or antibodies, is disclosed. The material comprises a porous matrix of fibers and a plurality of substantially spherical, solid particles having an average diameter of from about 0.1 to about 5 microns. The particles are retained and immobilized upon the fibers of the matrix. Preferably, the particles have on their surfaces a substance capable of reaction with the analyte in the sample, and the average diameter of the particles is less than the average pore size of the matrix. The device, in a preferred embodiment, comprises a substantially planar layer of the described material.

18 Claims, 3 Drawing Sheets

U.S. PATENT DOCUMENTS

| | | | |
|---|---|---|---|
| 4,338,094 | 7/1982 | Elahi | 435/810 X |
| 4,340,564 | 7/1982 | Harte et al. | 422/57 |
| 4,366,241 | 12/1982 | Tom et al. | 435/7 |
| 4,425,438 | 1/1984 | Bauman et al. | 436/824 X |
| 4,446,232 | 5/1984 | Liotta | 435/805 X |
| 4,472,353 | 9/1984 | Moore | 422/56 X |
| 4,472,498 | 9/1984 | Masuda et al. | 435/7 |
| 4,477,575 | 10/1984 | Vogel et al. | 422/57 X |
| 4,496,654 | 1/1985 | Katz et al. | 422/56 X |
| 4,515,889 | 5/1985 | Klose et al. | 435/4 |
| 4,517,288 | 5/1985 | Giegel et al. | 435/7 |
| 4,533,629 | 8/1985 | Litman et al. | 436/810 X |
| 4,540,659 | 9/1985 | Litman et al. | 435/7 |
| 4,541,987 | 9/1985 | Guadagno | 422/56 |
| 4,552,839 | 11/1985 | Gould et al. | |
| 4,558,013 | 12/1985 | Marinkovich | 436/809 X |
| 4,587,102 | 5/1986 | Nagatomo | 422/56 |
| 4,631,174 | 12/1986 | Kondo | 422/56 |
| 4,632,901 | 12/1986 | Volkirs et al. | 435/5 |
| 4,642,220 | 2/1987 | Bjorkman | 422/101 |
| 4,649,121 | 3/1987 | Ismail et al. | 435/14 X |
| 4,657,739 | 4/1987 | Yasuda et al. | 422/56 |
| 4,703,017 | 10/1987 | Campbell et al. | 436/525 X |
| 4,717,656 | 1/1988 | Swanljung | 435/7 |
| 4,740,468 | 4/1988 | Weng et al. | 436/501 X |
| 4,748,042 | 5/1988 | Linnecke et al. | 436/530 X |

SOLID PHASE ANALYTICAL DEVICE AND METHOD FOR USING SAME

BACKGROUND OF THE INVENTION

This application is a continuation of U.S. patent application Ser. No. 831,013, filed Feb. 18, 1986, hereby abandoned; which is a continuation-in-part of U.S. patent application Ser. No. 784,416, filed Oct. 4, 1985, now abandoned.

TECHNICAL FIELD

This invention relates generally to analytical devices and methods. More particularly, the present invention relates to a novel material useful in the performance of binding assays, to improved analytical devices, and to methods for conducting assays utilizing the material and the devices. The concepts of the present invention are especially advantageous in the performance of enzyme immunoassay of biological fluids and products such as serum, plasma, whole blood, urine, spinal and amniotic fluids, mucus and the like.

BACKGROUND ART

Various analytical procedures and devices are commonly employed in assays to determine the presence and/or concentration of substances of interest or clinical significance which may be present in fluids or other materials. Such clinically significant or interesting substances are commonly termed "analytes", and can include, for example, antibodies, antigens and the broad category of substances commonly known by the term "ligands". Particularly with respect to the diagnosis and treatment of disease or other conditions of the human body, the accurate determination, on a timely basis, of the presence or amount in biological fluids of certain analytes which are of clinical significance can have a profound influence on the ability of health care professionals to treat and manage pathological physical disorders, or to make an early and accurate determination of physiological conditions such as pregnancy.

One assay methodology which has been increasingly applied in the diagnosis of various disorders and conditions of the human body is the binding assay, and in particular the type of binding assay known as enzyme immunoassay (EIA). EIA techniques take advantage of the mechanisms of the immune systems of higher organisms, wherein antibodies are produced in response to the presence of substances (i.e., antigens) in the organisms which are pathogenic or foreign to the organisms. One or more antibodies are produced in response to and are capable of reacting with a particular antigen, thereby creating a highly specific reaction mechanism which can be advantageously utilized, in vitro, to determine that particular antigen.

Conventional EIA procedures involve a series of wet chemistry steps using liquid reagents, wherein an analyte in a sample biological fluid under assay, e.g., an antigen or antibody in a test sample of urine, whole blood or serum, is detected. In one type of EIA procedure, the analyte in the sample initially becomes bound to a corresponding antigen or antibody reagent which is introduced into the sample. Then, another antigen or antibody is introduced. This second antigen or antibody, however, is one which has been labeled or conjugated with an enzyme or other substance capable of producing or causing, often when reacted with or in the presence of an additional, suitable indicator reagent such as a chromogen or dye, a detectable response such as color development. The detectable response so produced can then be read and interpreted, visually or instrumentally, as an indication or measure of the presence or amount of the antigen or antibody present in the original sample.

Solid-phase EIA procedures are generally considered preferable for both antibody and antigen assays because of their safety, ease of use, specificity and sensitivity by comparison with heretofore-employed liquid reagent binding assay techniques such as radioimmunoassay (RIA), and other conventional wet chemistry methodologies. Moreover, the possibility of reading color development instrumentally, such as by use of a spectrophotometer, is a feature of many solid-phase EIA techniques which has resulted in their wide-spread use.

Thus, in one type of conventional solid-phase EIA "sandwich" assay, a test sample suspected of containing an antibody or antigen of interest is initially contacted by a solid, substantially inert plastic or glass bead or other support material which has been previously coated with a protein or another substance capable of reaction with the antigen or antibody to retain it on the surface of the support, either by immobilization of the antigen or antibody on the surface or by chemical binding therewith. A second antigen or antibody, which is usually conjugated (linked chemically) with an enzyme, is then added and this second species becomes bound to its corresponding antibody or antigen on the support. Following one or more washing step(s) to remove unbound material, an indicator substance, for example, a chromogenic substance reactive in the presence of the enzyme, is then added and, because of its sensitivity to the presence of the enzyme, produces a detectable color response. The development of the color response, its intensity, etc. can be determined visually or instrumentally, and correlated with the amount of antigen or antibody which was present in the sample.

Such assay techniques, and the use of the solid-phase bead or other types of supports for conducting the immunological reactions and changes necessary in such assays, are well known, but have not been without drawbacks. For example, the necessity of elaborate apparatus for conducting the assay and for containing the liquid reagents employed often results in substantial labor and equipment costs, especially for low-volume testing of individual samples. Moreover, the accuracy and reproducibility of such assays may often be less than optimum, since it is sometimes difficult to manufacture conventionally-coated solid supports and other apparatus associated with such assays so that, for a particular assay, all of the materials used therein are specifically designed to meet predetermined sensitivity and specificity requirements. Accordingly, a need exists for relatively simple, easy-to-use and comparatively inexpensive solid-phase materials and analytical devices which advantageously can be used in EIA procedures, and which are capable of producing rapid, sensitive and highly reproducible results comparable to conventional methodologies such as the aforedescribed, without the necessity for numerous, cumbersome wet chemical steps or complex instrumentation.

SUMMARY OF THE INVENTION

The present invention directly addresses the foregoing need, and provides, in one aspect, a novel material useful in the performance of a binding assay to determine the presence or amount of an analyte in a test sample, and an assay utilizing the material. In another aspect, the present invention provides an improved, solid-phase analytical device, and a binding assay using the device, which is highly advantageous over devices and assay methods of the prior art. In yet another aspect, the present invention provides unique, on-board procedural controls for use with solid phase analytical devices. In yet another aspect, the present invention provides barrier means for restricting fluid flow in solid-phase analytical devices.

The novel material of the invention comprises a porous matrix of fibers and a plurality of substantially spherical, solid particles having an average diameter of from about 0.1 to about 10 microns. Preferably from about 0.1 to about 10 microns, the particles being retained and immobilized within the matrix upon the fibers. In a preferred embodiment, the particles have on their surfaces a substance capable of reaction with the analyte in the sample. In a further preferred embodiment, the average diameter of the particles is less than the average pore size of the matrix.

The improved device of the invention comprises a substantially planar layer of the aforedescribed material, which forms a reaction matrix for a binding assay. The substantially planar layer has a first, sample-contacting surface and a second surface opposed to the first surface. The substantially planar layer is disposed in the device such that, when the device is used in the performance of a binding assay, at least a portion of the sample contacting the first surface passes through the substantially planar layer to the second surface. Preferably, the assay device of the invention additionally comprises filtering means disposed in relationship to the first surface of the substantially planar layer, such that, when the device is in use, sample fluid passes through the filtering means prior to contacting the first surface. It is further preferred that the device of the invention comprise absorbent means (for absorbing fluid passing through the substantially planar layer).

The concepts of the invention are advantageous not only in the performance of binding assays to determine the unknown presence or concentration of various analytes in test samples, but also to provide on-board controls for solid phase assay devices. As described in more detail, infra, a preferred solid-phase analytical device in accordance with the invention can incorporate therein assay controls, such as a visible positive control area for displaying a negative result which enables unambiguous interpretation of test results in a visual assay system. Also, for example, a preferred procedural control device utilizing the concepts of the invention can comprise the material of the invention, the material having within its porous matrix of fibers a substance capable of producing a detectable response to an analyte in a test sample under analysis.

The barrier means of the invention comprises a barrier material interposed between the reaction matrix and the absorbent means of a solid phase analytical device for restricting fluid entering the absorbent means from re-contacting the reaction matrix.

In addition, according to the present invention improved methods for performing a binding assay, utilizing the material and device of the invention, are provided. In one such preferred method, a sample containing an analyte, e.g., antigen or antibody, is contacted with a reaction matrix made from the material. The analyte becomes bound to the reagent upon the particles retained within the material of the matrix; the matrix is then contacted with a second "labelled" reagent also capable of becoming bound to the analyte which is bound by the reagent retained within the matrix. Alternatively, the second reagent can be an unlabelled antibody, followed then by addition of labelled substance or reagent direction against the antibody (Amplification or Indirect immunoassay). Thereafter, unbound material is removed. e.g., by washing, and the device is contacted with an indicator substance which, in the presence of the "label" of the second reagent, produces a detectable response which is indicative of the presence and/or amount of the analyte in the sample. Such a detectable response can be read visually or instrumentally, and can advantageously be a color response, most desirably in the form of the visible appearance of a "+" or "−" sign to indicate the result of the assay. Particularly if only positive or negative results, respectively, from the assay are necessary or desired. Alternatively, quantitative or semi-quantitative results can be obtained by visually or instrumentally reading the detectable response.

DETAILED DESCRIPTION OF THE INVENTION

The novel material of the present invention, and devices produced therefrom, although applicable to many types of analysis, are especially advantageous when used in immunoassays, to improve conventional solid-phase immunoassay techniques for performing colorimetric or other EIA of biological fluids, such as previously described. Moreover, devices produced in accordance with the invention are relatively easy to use, and require fewer procedural steps and less complex assay technique, by comparison with prior art assays, and also provide the additional advantage of rapid quantitative, semi-quantitative or qualitative results for testing of unknown samples. The material and devices are additionally adapted for advantageous use as controls, e.g., to assess the accuracy and reliability of such assays. Moreover, during manufacture, devices of the invention can be relatively easily made. Assays utilizing such devices of the invention have also been found to be highly sensitive to various levels of analytes. The foregoing advantages, as well as other advantages, will be apparent from the detailed description of the invention as set forth herein.

The concepts of the present invention are applicable to various types of binding assays. Schematic representations of examples of several such types of assays for antigen and antibody analytes can be set forth as follows. However, it will be appreciated that one skilled in the art can conceive of many other types of assays, including analytes other than antigens or antibodies, to which the present inventive concepts can be applied.

1. Direct Assays

A. Antigen (Ag) Assay

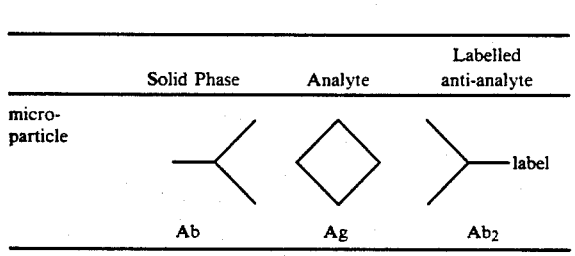

Ab, may or may not be the same as Ab₂ and may consist of a variety of monoclonal antibodies or polyclonal antibodies.

Examples of antigen analytes determinable according to the invention using foregoing reaction scheme include, without limitation, Strep-A, beta-hCG and hepatitis B surface antigen (HBsAg).

B. Antibody (Ab) Assay

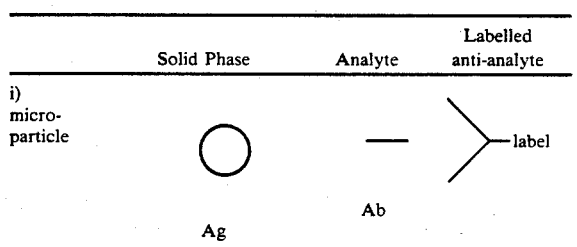

Analyte examples (not limitative):
a-HTLV-III;
a-HBc-IgM;
a-Rubella

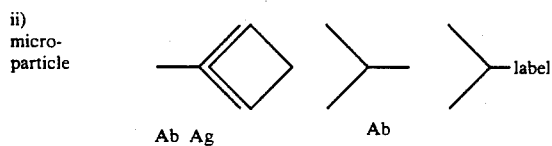

Analyte example: a-HAV-IgM

2. Indirect Assays

Antigen Assay

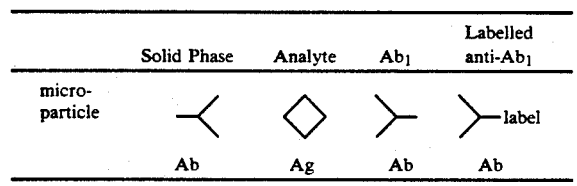

This is a group of assays where the label is not directed against the analyte. In this embodiment, anti-Ab₁ may be directed against Ab₁ in general, or may be directed against one or more functional groups incorporated into Ab.

It is also desireable, in some cases, to capture the analyte directly on the solid phase, as follows:

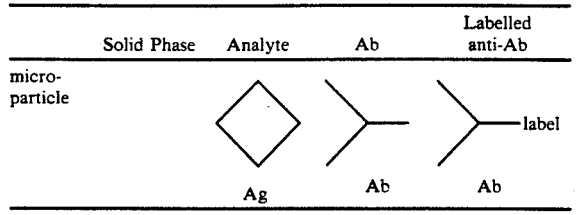

3. Competitive Assays

Antibody Assay

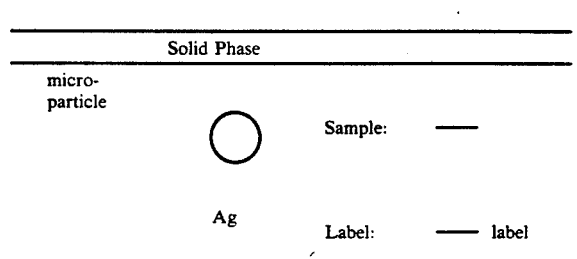

In assay scheme 3, both the sample and the label are directed against the antigen on the solid phase. The amount of label bound reflects the amount of antibody in the sample.

Figure 1:
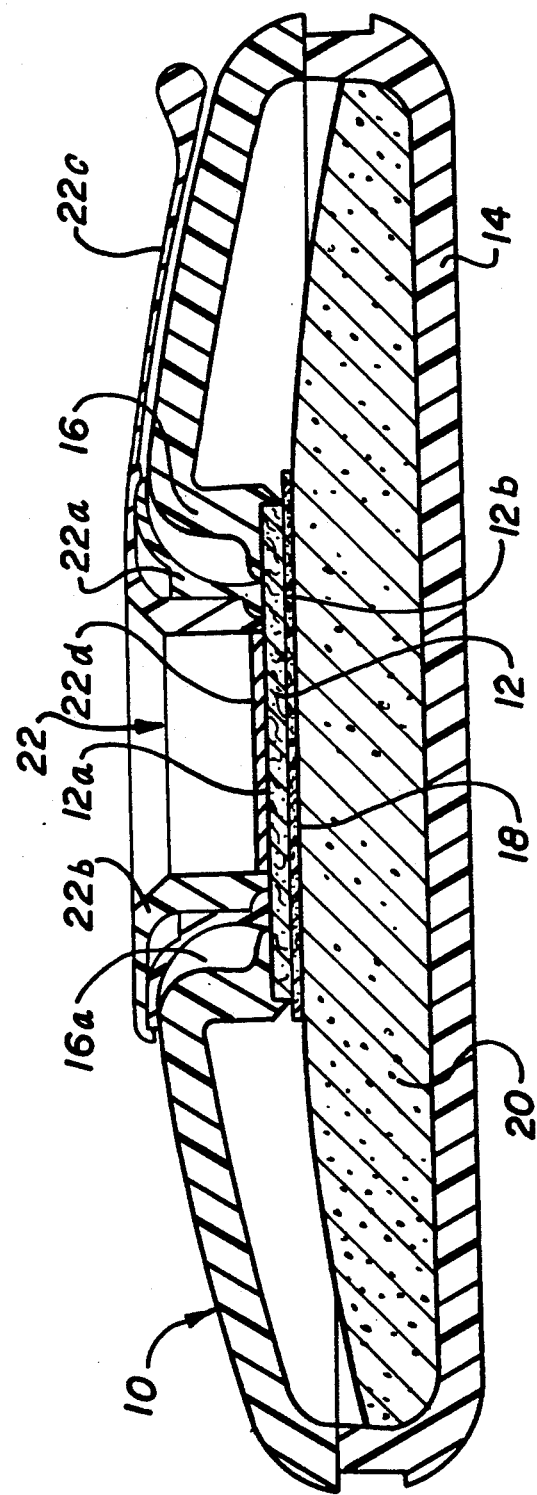
FIG. 1 is a side view in partial cross section of an analytical device in accordance with the present invention.
Figure 2:
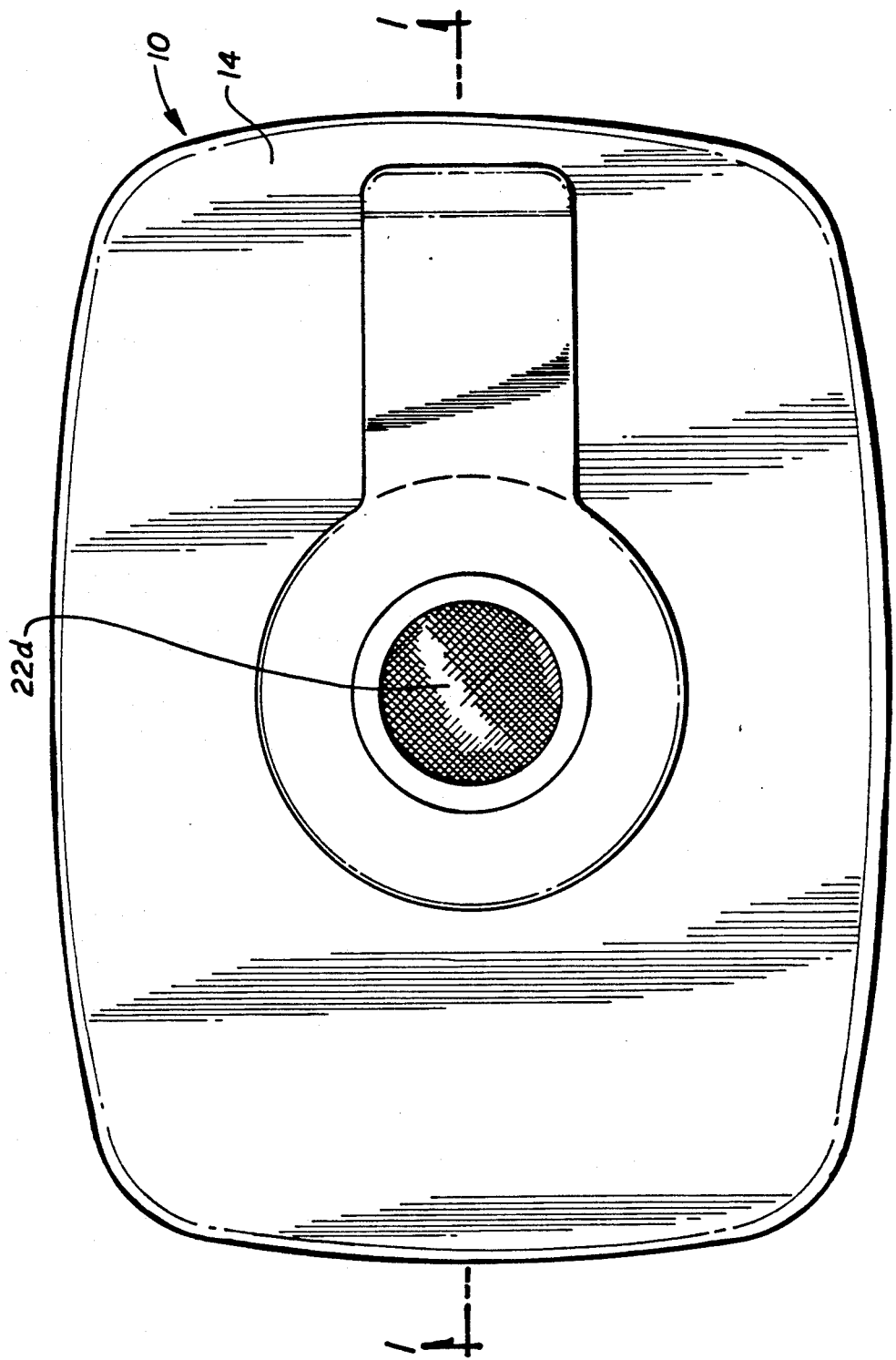
FIG. 2 is a top plan view of the device of FIG. 1.

Referring to FIGS. 1 and 2 of the drawings, a preferred embodiment of the analytical device of the present invention is shown generally at 10. The preferred device 10 includes a substantially planar, generally circular, disk-shaped reaction matrix 12. The matrix 12 comprises the novel material of the invention, as described herein, and is disposed within the device 10 such that within the matrix 12 the various chemical reactions and changes necessary to a binding assay can take place when the device 10 is used (as described, intra, in detail) in the performance of such assays, to determine the presence or amount of analyte(s) in a sample under analysis. The matrix 12 has a sample-contacting surface 12a and a surface 12b opposed therefrom; a preferred composition of the matrix 12 is described in greater detail in the examples, infra.

Figure 3A:
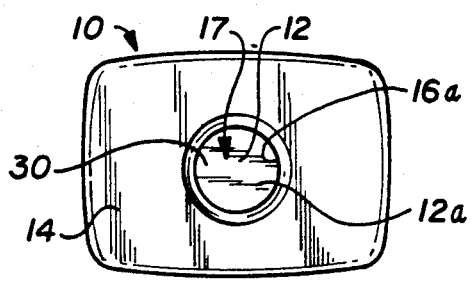
FIGS. 3A, 3B and 3C are top plan views of a particularly preferred embodiment of the device of FIG. 1.

The preferred device 10 additionally includes a carrier 14 within which the matrix 12 is disposed. The carrier 14 can be made of any suitable material such as plastic, metal or other rigid or semi-rigid substance. Especially preferred as a material for the carrier 14 is a plastic commercially known as "ABS", and available from the Monsanto Company, St. Louis, Mo. In the preferred embodiment shown, the carrier 14 completely surrounds the matrix 12 and functions as a support and holder therefor. In order to accomplish this function, the carrier 14 has a generally circular flange 16 for supporting and holding tightly the matrix 12. As best shown in FIG. 3a, a fluid chamber 17 for receiving a fluid sample and reagents used in the performance of an assay is defined in the device 10 by a sidewall formed by the outer wall surface 16a of the flange 16 and a base wall formed by the sample-contacting surface 12a of the matrix 12.

The preferred device 10 further comprises absorbent means 20 disposed in the carrier 14, as shown, for absorbing fluids during use of the assay device. The absorbent means 20 of the device 10 can comprise one or more layers of material and is in physical contact, as shown, with the barrier material 18, when used, or with the reaction matrix 12. This especially advantageous feature enables excess fluid, during the performance of an assay using the device 10, to be easily absorbed, as necessary, after passage of such excess fluid from the reaction matrix 12 during the assay procedure. The absorbent means 20 can be virtually any moisture or fluid-retaining material, e.g., that available from James River, and designated "105 point" or "50 point", or, as is especially preferred, a combination of one of more layers of each of the foregoing.

In another aspect of the invention, barrier means are provided for restricting fluid flow in solid phase analytical devices. This aspect is particularly advantageous when used in solid phase analytical devices having a permeable reaction surface or matrix, or filter layer, and an absorbent layer for absorbing fluids used in the device to permit the flow of fluids from the reaction surface to the absorbent means or layer while preventing the back flow of fluids from the absorbent layer to the reaction matrix.

As shown in FIG. 1, the barrier means comprises a layer of barrier material 18 extending under the matrix 12 and within the carrier 14. The barrier material 18 is in contact with the surface 12b of the matrix 12, and functions, when the device is in use, to restrict fluid passing through the matrix 12, to and through the surface 12b, and into the layer 18, from re-contacting the surface 12b. It is to be appreciated that although it is most preferred in a device of the invention to utilize the layer 18 as a fluid restrictive layer, to help to prevent or eliminate "background" interference in the matrix 12, this feature is not essential or critical to the basic functions or concepts of the matrix 12, and usually can be omitted from the device if desired. If omitted, the device generally will perform satisfactorily in an assay, but possibly with less sensitivity (diminished detectable response).

The layer 18 can comprise any suitable material capable of restrictive, substantially "one-way" flow of fluid or moisture. Examples of especially suitable materials for this purpose are polyethylene weave materials manufactured and sold by Ethyl Visqueen Corp., Baton Rouge, La. under the designations "X-6057" (1.0 mil) and "X-6108" (1.25 mil) as well as those materials described in U.S. Pat. Nos. 3,929,135 and 4,342,314.

It is to be appreciated that in addition to the capability of the preferred device 10, as described infra, to produce a visually-readable response such as color development indicative of an analyte in a test sample, instrumental determination can be made of a detectable response therefrom, e.g., corresponding to the reflectance of visible light, or intensity of fluorescence or the like, produced by the matrix 12 as a result of the chemical and biological reactions and changes which occur therein when an assay is performed. Accordingly, the detectable response from the device 10 can be measured by, for example, a conventional spectrophotometer. For example, if the detectable response in the matrix 12 produced by the reactions and changes during a particular assay is one wherein a color is developed, and wherein increasing color development indicates an increasing level of a particular analyte in a test sample undergoing analysis, then a diminishing level of light reflected from the matrix 12 to the spectrophotometer corresponds to that increased level of analyte in the sample. The interpretation of such results is capable of being accomplished in ways well known to those skilled in the art, such as by conversion of analog signals generated by the detector of the spectrophotometer to digital information using largely conventional electronics. Such electronics are also well known to those skilled in the art, and are capable of producing a human-readable signal from such digital information which corresponds or correlates to the presence and/or amount of analyte in the test sample.

Figure 5:
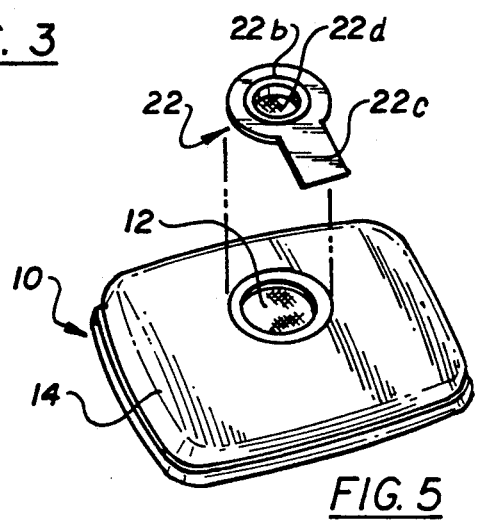
FIG. 5 is a perspective view of the device of FIG. 1, showing the pre-filter removed from the body of the device.

Referring now in more detail to FIGS. 1, 2 and 5 of the drawings, the particular preferred embodiment of the analytical device 10 of the invention further includes filtering means 22 disposed over surface 12a of the reaction matrix 12. The filtering means 22 is press-fitted into the carrier 14 by means of a retaining ring 22a, and preferably has a removable portion 22b having a handle portion 22c. The means 22 is further composed, for example, of a suitable porous, fibrous material 22d such as a glass or cellulose filter membrane in a plastic surround; especially preferred are "LYDAIR TM Grade 254" from Lydall, and "GF/F" or "GF/D" from Whatman, either singly or in combination. When the device 10 is used to perform an assay, the means 22 can perform various functions. Depending upon the type of assay being performed and the nature of the test sample, the means 22 can perform such functions as a reservoir to retain sample or slow the passage of sample or reagents to the reaction matrix 12; as a vehicle to retain reagents, e.g., lyophilized reagents, to be used in an assay; and as a "prefilter" to remove extraneous articulate matter in a sample, or, for example, to separate and to hold blood cells from a whole blood sample while allowing plasma to pass through. In addition, as shown in FIG. 5, if the filter means 22 is at least partially removable from the device 10 (a feature preferred but not essential in the present invention), then during performance of an assay using the device 10, the removable portion 22b of the filter means 22 can be removed, as desired, during a step of the assay in order to remove material which may be retained therein, or to expose the reaction matrix 12 for the addition of reagents or to read a detectable response therefrom. In this case the membrane portion of the filter means 22 is an integral part of the removable portion thereof 22b.

In accordance with the invention, the material useful in the analytical device and methods of the invention comprises a porous, fiber matrix. By "porous" is meant that the matrix is composed of a material into which fluids can flow and can easily pass through. In the material of the present invention, the property of porosity can be achieved simply by selection of an appropriate raw material, such as glass, cellulose, nylon or other fibrous material well known to those skilled in the art.

For example, an especially preferred material for use is "Whatman GF/D" glass fiber filter paper, which has a nominal thickness of 0.032 inch. The thickness of such a material is not critical, and will be a matter of choice for the routineer, largely based upon the properties of the sample (and analyte) being assayed, such as its fluidity and the necessity to retain enough of the sample within the material for a long enough time to enable sufficient binding of the analyte.

In addition, according to the invention the fibrous material preferably has a plurality of substantially spherical, solid particles having an average diameter of from about 0.1 to about 10 microns or more, most preferably from about 0.1 to about 5 microns, retained and immobilized upon the fibers of the material. By "retained and immobilized" is meant that the particles, once upon the fibers of the material, are not capable of substantial movement to positions elsewhere within the material, (i.e., to other fibers), or cannot be removed completely from the material without destruction thereof. The mechanism by which the particles are so retained and immobilized is not known, but may be due to physical surface attractions between the fibers and the particles, and/or between the particles themselves. The particles can be selected by one skilled in the art from any suitable type of particulate material known generally as "microparticles"; such particles are typically composed. e.g., of polystyrene, polymethylacrylate, polypropylene, latex, polytetrafluoroethylene, polyacrylonitrile, polycarbonate or similar materials. Whatever type of microparticles is selected for use in the invention, it is important that the substance or substances of which the particles are composed be capable of holding on the surface of the particles a substance capable of reaction with an analyte in a test sample, e.g., antibody or antigen, or a combination thereof, or be itself capable of holding an analyte on the surface of the particles. Moreover, the size of the particles is not critical, and so long as the average diameter of the particles is substantially within the aforestated range (although it is preferred that the average diameter of the particles be smaller than the average pore size of the fibrous matrix), any type of particles having the foregoing properties is suitable for use.

The material and analytical devices provided by the invention, it is to be appreciated, can be advantageously employed in a wide variety of otherwise well-known assay techniques and procedures, and are not limited in application to the specific immunoassay techniques described in detail herein. They can thus be used in so-called "competitive binding" assays or similar binding assay procedures, and in addition, can be employed in other assays such as typical enzyme assays for such analytes as glucose, uric acid or the like, which are not immunoassays but which can advantageously be carried out by initially retaining at least one reagent used in such assays upon the particles within the material or reaction matrix of a device of the invention. It will be readily apparent to those skilled in the analytical arts that the instant invention can be profitably applied to a wide variety of uses in various types of assay procedures, and thus is in no way limited to the specific details of the assays and procedures described herein.

The novel material, and analytical devices, produced in accordance with the principles of the instant invention can, however, be especially advantageously employed in enzyme immunoassays, particularly so-called "sandwich" and indirect enzyme immunoassays. Such assays can be performed using the material and devices of the invention in a manner which is substantially more simple than typical "bead" or other assays of the prior art which require relatively elaborate, time-consuming and costly equipment and materials. Such assays also have been found to be capable of surprising sensitivity. A generalized example for one presently preferred "sandwich" immunoassay procedure utilizing the material of the instant invention is as follows:

Step a) Retention of antibody or antigen upon the particles in the material, forming a reaction matrix, as previously described;

Step b) Application of a test sample containing antigen or antibody to be determined to the matrix;

Step c) Application of an enzyme-conjugated antibody or antigen to the antigen or antibody of Step b);

Step d) Washing, to remove unbound material; and

Step e) Application of an indicator substance which, in the presence of the enzyme portion of the conjugate of Step c), Produces a detectable color or other response in the reaction matrix.

A more detailed discussion of how such "sandwich" assay procedures can advantageously be carried out using the device of the present invention is set forth in the examples, infra.

In accordance with the present invention, a detectable response is produced in the material or reaction matrix of an analytical device; the response is one which is indicative of the presence and/or amount of an analyte in a sample under analysis. Such a detectable response, in preferred embodiments of the invention, can be color development following a series of assay steps, such as those previously described, or can be any number of responses well known in the analytical arts and used for similar purposes. For example, the response produced can be one of fluorescence, provided appropriate reagents are employed in the assay, as is well known to those skilled in the art. The response can be also chemiluminescence, or any of a variety of radiative energy responses (e.g., radioactive emissions) detectable either visually, or instrumentally by various known equipment. Thus, it is to be especially appreciated that in use of the materials and devices of the invention, many different types of detectable responses are possible and desirable and the inventive concepts are not limited thereby.

In another aspect of the inventive concepts, "on-board" control areas are provided on solid phase analytical devices to simultaneously display detectable responses corresponding to a positive control (which will display a detectable response indicative of a valid assay result, regardless of the presence or absence of an analyte of interest in a test sample), a negative control (which will display a detectable response change only if the assay results are invalid) and the sample analyte in a single analytical device reaction surface. In this aspect of the invention, the same volume of a test sample and assay reagents are simultaneously placed in contact with the procedural controls and test areas, thereby avoiding the necessity of separate control tests as generally practiced in the art. Although this aspect of the invention will hereinafter be described in detail in connection with the presently particularly preferred reaction matrix and analytical device as heretofore described, it will be apparent to those skilled in the art that this aspect of the invention may be similarly employed with any analytical device having a reaction surface capable of simultaneously displaying a plurality or multiplicity of reaction results. Such other types of reaction surfaces include, for example, coated or uncoated fiber matrices, filters or membranes, relatively planar solid surfaces and the like.

Referring now to FIGS. 3A, 3B, 3C, 4A, 4B and 4C, on-board negative and positive control areas 30 and 32, respectively, are preferably provided on the reaction surface or matrix 12 of the analytical device 10. The negative and positive control areas may function in a quantitative manner thereby functioning as negative and positive assay reference controls, or may function in a qualitative manner thereby functioning as procedural controls indicating the validity of procedures and reagents used in the performance of an assay. As used herein, the term "control" includes both quantitative and qualitative embodiments. Negative control area 30 is formed by maintaining the control area 30 of the matrix 12 free of substances which Will retain the enzyme label or other signal response material during the normal use of the device 10 in the performance of a binding assay, as described herein. Positive control area 32 is formed by providing a substance capable of binding the enzyme label or other signal response material within the control area 32 of the matrix, regardless of the presence or absence of the analyte of interest in a test sample. As used in connection with the particularly preferred reaction matrix as previously described, positive control area 32 may be formed by coating the microparticles within the control area 32 with the analyte, or other substances capable of binding or retaining the enzyme label within the area 32 during performance of a binding assay. In addition, one or more analyte binding area(s) 34 are provided on the matrix 12 for binding or retaining the analyte of interest from a test sample on the area 34 during the performance of a binding assay. The analyte binding area(s) 34 may be formed in the particularly preferred reaction matrix material described herein by coating the microparticles within the area(s) 34 of the matrix 12 with a substance, such as antigen or antibody, capable of binding the analyte.

Figure 3B:
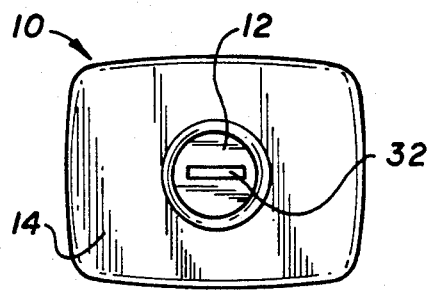

The positive control area 32 and the analyte binding area(s) 34 may be provided in any configuration which facilitates ease of use of the device 10 in the performance of a binding assay. However, it is presently preferred to provide the positive control area and the analyte binding area in an interactive configuration in which the positive control area interacts with the analyte binding area upon the occurrence of a positive test result to form a first representational symbol having a known meaning to the user, and the positive control area acts alone upon the occurrence of a negative test result to form a second representational symbol having a known meaning to the user different from that of the first representation symbol. Interactive positive control and analyte binding areas are best shown in the particularly preferred embodiment of FIGS. 3A, 3B and 3C, wherein the positive control area 32 is formed in the shape of a rectangular bar or "−" sign, while the analyte binding areas 34 are formed in the shape of rectangular bars on opposite sides of, and oriented perpendicularly with respect to, the positive control area 32. Accordingly, in use of the device of FIGS. 3A, 3B and 3C, a positive test result obtained from the proper use of the device 10 will result in a detectable response, in the shape of a "+" sign, in both the positive control area 32 and the analyte binding areas 34, as shown in FIG. 3C, indicating a "+" or positive test result to the user. A negative test result obtained from the proper use of the device 10 will result in a detectable response, in the shape of a "−" sign, in only the positive control area 32, as shown in FIG. 3B, indicating a "−" or negative test result to the user. If the binding assay is improperly conducted, or if reagents used in the assay function improperly, no detectable response is obtained in either the positive control area 32 or the analyte binding areas 34, as shown in FIG. 3A, indicating an invalid test result. In addition, any detectable response in the negative control area 30, such as may be caused by non-specific binding or failure to properly perform washing steps in the performance of the assay, may be indicative of an invalid test result. The configuration of FIGS. 3A, 3B and 3C is presently particularly preferred since it provides immediate information to the user in unambiguous, symbolic form as to the positive (+) or negative (−) nature of the test result, and as to the validity of the assay.

Figure 4A:
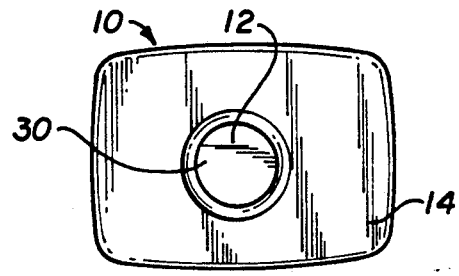
FIG. 4A, 4B and 4C are top plan views of an alternate embodiment of the device of FIG. 1.
Figure 4B:
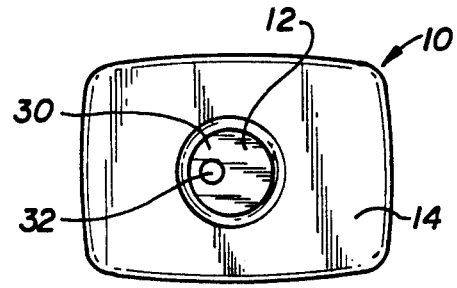
Figure 3:
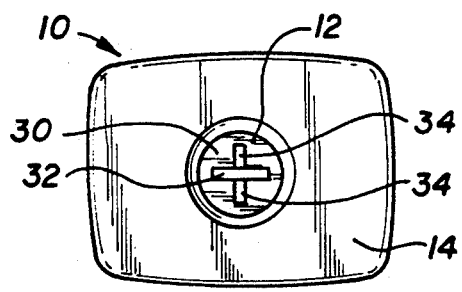
Figure 4:
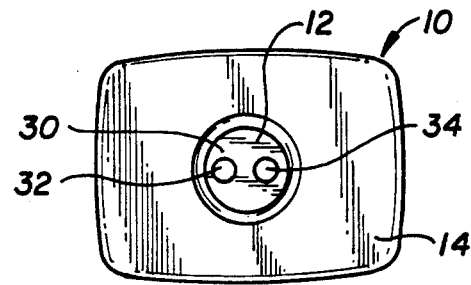

Alternatively, the procedural control areas and the analyte binding areas may be provided in other configurations, as desired. In the alternate embodiment of FIGS. 4A, 4B and 4C, the positive control area 32 and the analyte binding area 34 are formed in the shape of dots, as shown. Thus, a positive test result is indicated by the presence of two dot-shaped detectable response areas, as shown in FIG. 4C, a negative test result is indicated by the presence of a detectable response only in the positive control area 32, as shown in FIG. 4B, and invalid test result is indicated by the lack of a detectable response as shown in FIG. 4A. In yet another configuration the negative control area surrounds the positive control area and the analyte binding area. Other equivalent configurations for the negative control area 30, the positive control area 32 and the analyte binding area(s) 34, such as other symbols, numbers and the like, will be readily apparent to those skilled in the art.

EXAMPLES

The following examples illustrate preferred ways of making and using the novel material of the present invention, and analytical devices using the material, as well as assay procedures utilizing them. The analytical devices made had substantially the overall shape and appearance of the device shown and described herein with reference to FIGS. 1 and 2 and were prepared and utilized in assays according to the invention using the following procedures. However, the examples are intended to be only illustrative, and in no way to be construed as placing limitations upon the scope of the invention, which scope is defined solely by the appended claims.

Unless otherwise indicated, all percentages expressed herein are by weight.

EXAMPLE 1

Preparation of Antibody-Coated Microparticles 100 microliters of carboxylate-modified microparticles (2.5% solids; 0.45 microns average diameter; Commercially available from polyscience and Seragen) were added to 1.0 milliliters (ml) of methyl ethyl sulfonate (MES) buffer (5 millimolar (mM), pH 4.75) and 75 microliters of antibody solution (beta-hCG) (2 milligrams per milliliter (mg/ml)). The solution was stirred and then 100 ml of 1-Ethyl-3(3-Dimethylaminopropyl) carbodimide HCl (EDAC) (2 mg per 10 ml $H_2O$) were added. The solution was stirred overnight at 2-8 degrees C., after which the microparticles were isolated by centrifugation, washed twice with 0.1% "TWEEN-20" solution, and resuspended in "PBS" Phosphate Buffered Saline (0.01M $KH_2PO_4$; 0.15M NaCl: pH 7.2) to yield a 0.125% solution. After resuspension in PBS, the particles were stored at 2-8 degrees C., for subsequent use in the following procedures.

EXAMPLE 2

Preparation of Solid-phase Reaction Matrix 50 microliters of the antibody-coated microparticles from Example 1 were added dropwise to the center of a Whatman GF/D glass filter: 100 microliters of pig sera were then added and the filter and microparticles incubated for 30 minutes in a humidity chamber at room temperature. After this time, the filter, now containing the microparticles, was washed three times in 300 microliters of PBS buffer. The filter was then stored in a humidity chamber until it was used in the following immunoassay example. The microparticles were observed, by scanning electron microscopy, to have been irreversibly trapped or agglomerated on the glass fibers of the filter material.

It is to be noted that, in addition to the techniques described in the foregoing example, antibody (or antigen) may be attached to the particles by a variety of methods: e.g., adsorption or use of various chemical activators. Also, it is to be appreciated that the particles can be added to the fibrous matrix after, for example, animal sera has been added, and that the use of such sera is not of critical importance. Therefore, the order of addition of the particles to the matrix and treatment thereof after or before incorporation into the matrix is not critical to the present invention. Moreover, it will be appreciated that coated fibrous materials, such as polystyrene-coated glass, can be used in place of the glass filter matrix material specifically described herein, and the advantages of the invention can also be realized thereby.

EXAMPLE 3

Immunoassay protocol (Determination of beta-hCG)

The glass fiber material, containing the antibody-coated microparticles as previously described, was cut into substantially circular "disks", and the disks, forming reaction matrices, placed in contact with a blotter material in order to absorb excess fluid from solutions used in the assay. Thereafter, five drops of test samples of human urine (about 280 microliters), containing zero, and 50 and 100 mIU/ml levels of beta-hCG (Table 1, infra), were added to each matrix after passage of the sample drops through a prefilter situated above each matrix. Three drops of an antibody-enzyme conjugate (Table 1, infra) were then added to each matrix through the prefilter, and each matrix was incubated at room temperature for about two minutes. The prefilter was next removed, and 1.0 ml of a detergent wash solution was added to each matrix to remove any excess antibody-enzyme conjugate. Then, one drop of a chromogen indicator (Table 1, infra) was added to each matrix, and after two minutes each matrix was checked visually for color development. Color development was observed for the test samples which contained beta-hCG, and the absorbance of light correlating to the color development was determined instrumentally using a conventional spectrophotometer. The results are set forth in the following table.

TABLE 1

Data for beta-hCG: Horseradish Peroxidase (HRPO) antibody-enzyme conjugate/3,3',5,5',- tetramethyl benzidine (TMB) chromogen (Absorbance after two minutes at 650 nanometers (nm))

| (hCG) mIU/ml in urine samples | Instrumental | Visual |
|---|---|---|
| 0 | 0.0159 | Not visible |
| 50 | 0.0852 | Visible |
| 100 | 0.2617 | Visible |

TABLE 2

Data for beta-hCG: Alkaline Phosphatase

TABLE 2-continued antibody-enzyme conjugate/Bromo-chloro indole phosphate nitro-blue tetrazolium chromogen. (Absorbance after two minutes at 650 nanometers)

| (hCG) mIU/ml in urine samples | Instrumental | Visual |
|---|---|---|
| 0 | 0.0057 | Not visible |
| 50 | 0.0872 | Visible |
| 100 | 0.1584 | Visible |

The foregoing antibody-enzyme conjugates were prepared generally in accordance with the following references: HRPO: Nakane, P. K. and Kawaoi, A., The Journal of Histochemistry and Cytochemistry, 22 (12) 1084–1091 (1974): Alkaline phosphatase: Prepared by slight modifications to a Glutaric dialdehyde procedure, available from Boehringer Mannheim GmbH.

Urine samples from twelve non-pregnant and six confirmed pregnant women were tested using the HRPO-antibody enzyme conjugate, described supra, and substantially the procedure described in Example 3. Twelve samples from the non-pregnant individuals produced no visible color in the reaction matrix; i.e., all absorbances were less than 0.050, below which threshold no color can easily be visualized. Samples from all of the six pregnant individuals produced visible color upon testing.

EXAMPLE 4

Preparation of beta-hCG Procedural Control 1.0 ml of microparticles (as previously described, 0.125% solids), having antibody to beta-hCG attached to their surfaces, were reacted with 14.0 microliters of beta-hCG solution (1.0 mg/ml). The solution was stirred for three hours at room temperature, and then stored at 2–8 degrees C. until needed. No further washing of the particles was required.

50 ml of the foregoing procedural control microparticles, having beta-hCG bound to their surfaces, were diluted to various concentrations and applied to the glass fiber filter material previously described, in the same manner as the antibody-coated microparticles had been applied (described supra). The activity of each dilution was then checked by adding two drops (about 100 microliters) of HRPO-antibody enzyme conjugate, incubating for five minutes, washing with 1.0 ml of a detergent wash solution and then developing color by the addition of one drop (about 50 microliters) of TMB solution. The absorbance of each control was then measured using a conventional spectrophotometer, as set forth in the following table.

TABLE 3

| Dilution of Stock Solution | Absorbance After Two Minutes at 650 nm |
|---|---|
| 1:8 | 0.7118 |
| 1:32 | 0.2358 |
| 1:64 | 0.0983 |

The absorbance of the procedural control at a 1:32 dilution was found to be approximately equal to that of a 100 mIU/ml beta-hCG standard.

EXAMPLE 5

Bacteriological Testing-Heterologous Bacteria

Assays for Strep A antigen, and assays for antigens for the various organisms listed in the following table, were performed using devices of the invention as previously described. The protocol of the assays can be summarized as follows:

1. A pre-prepared bacterial swab sample (prepared by a well-known technique) was placed into solution and pipetted onto the filter assembly over the reaction matrix of the device. The sample was allowed to pass through the filter.
2. Two drops (about 100 microliters) of antibody-enzyme conjugate were added, and allowed to pass through the filter.
3. The filter was then removed and the matrix washed with 10-12 drops (about 500 microliters) of PBS Buffer.
4. One drop (about 50 microliters) of TMB were added, and color development in the matrix read after about 2 minutes incubation at room temperature.

The absorbance of 650 nanometer light reflected from the matrix was then determined, using conventional reflectance apparatus, as a result of assays performed as aforedescribed on samples which contained the microorganism antigens listed in the following table.

TABLE 4

Assays for Heterologous Bacteria

| Microorganism[a] | Absorbance[b] |
|---|---|
| *Serratia marcescens* | 0.040 |
| *Klebsiella pneumoniae* | 0.032 |
| *Pseudomonas aeruginosa* | 0.045 |
| *Neisseria meningitidis* | 0.034 |
| *Neisseria sicca* | 0.036 |
| *Haemophilus influenzae* | 0.051 |
| *Staphylococcus aureus* Cowan I | 0.084 |
| *Staphylococcus aureus* Cowan II | 0.049 |
| *Bordetella pertussis* | 0.041 |
| *Candida albicans* | 0.032 |
| *Streptococcus pneumoniae* | 0.056 |
| *Streptococcus agalactiae* (Group B) | 0.054 |
| *Streptococcus equisimilis* (Group C) | 0.063 |
| *Streptococcus faecalis* (Group D) | 0.047 |
| *Streptococcus cariis* (Group G) | 0.101 |
| *Streptococcus pyogenes* (Group A) | 1.392 |
| Negative Control | 0.049 |

[a]Microorganisms were assayed at a concentration of $10^6$ CFU per test.
[b]Absorbance at 650 nanometers.

EXAMPLE 6

Solid Phase Evaluation; Use of Various Reaction Matrix Materials According to the Invention Zero concentration and 250 mIU/ml concentration beta-hCG-containing urine samples were assayed as previously described (Example 3) using microparticles which had been incorporated in various fibrous matrix materials, according to the invention. The materials listed in the following table were of different pore sizes and flow rates. The Whatman GF/D material was also pretreated before addition of the particles. An HRPO conjugate was used. In each assay, color development, indicating success of the assay, was visually observed, and absorbance readings were taken at 650 nanometers. The results are compiled in the following table.

TABLE 5

| Matrix | 0 mIU/ml | 250 mIU/ml | *Pore Size | **Flow-rate |
|---|---|---|---|---|
| 1. Whatman GF/D | .0038 | 0.2284 | 2.7 | 41 |
| 2. Whatman GF/D precoated with polystyrene (4.4 mg/ml THF) | .0057 | 0.2603 | 2.7 | 41 |
| 3. Whatman GF/D precoated with pig sera | .0058 | 0.3883 | 2.7 | 41 |
| 4. Whatman 934-AH | .0041 | 0.2801 | 1.5 | 47 |
| 5. Whatman GF/C | .0008 | 0.1855 | 1.2 | 100 |
| 6. Whatman GF/A | .0059 | 0.1674 | 1.6 | 62 |
| 7. S + S#30 Glass*** | .0036 | 0.3331 | — | — |

*Microns
**Seconds/100 ml at 10 cm head.
***Schleicher and Schnell

The foregoing data indicates that a variety of raw fibrous materials can be used in the novel material and reaction matrices of devices of this invention. Such alternative raw materials can be used after pretreatment with protein sera or polystyrene (hydrophilic or hydrophobic) in order to change somewhat the characteristics of the material, as desired (e.g., flow rate).

EXAMPLE 7

Effect of Particle Size

Particles ranging in size from 0.19 to about 3.0 microns (average diameter) were added to samples of matrix materials (Whatman GF/D)). The amount of antibody per sample was maintained at about 3.0 micrograms, and zero and 100 mIU/ml beta-hCG-containing urine samples were assayed as previously described, using an alkaline phosphatase conjugate. Absorbance readings were taken at 650 nanometers. The results are set forth in Table 6.

TABLE 6

| Average Diameter of Particles (microns) | Zero beta-hCG | 100 mIU/ml beta-hCG |
|---|---|---|
| 0.19 | .0065 | .1037 |
| 0.50 | .0050 | .1500 |
| 0.90 | .0076 | .0825 |
| 3.0 | .0061 | .1227 |

The above results demonstrate that particles ranging in size from 0.19 to about 3.0 microns in diameter are particularly effective, and thus preferred. Particles within the range of from about 0.1 to about 5 microns, however, are suitable for use in the invention. Also, since the pore size of the GF/D filter material is about 2.7 microns, the data shows that particles much smaller, or larger, than the average pore size of the fibrous matrix material can be used.

EXAMPLE 8

Rapid Assay for beta-hCG

An advantageously rapid, and procedurally simple assay for beta-hCG was conducted using an analytical device which had been produced in accordance with the present invention, as previously shown and described with reference to FIGS. 1 and 2. The assay protocol was as follows.

Five drops of a patient urine specimen were applied from a medicine dropper to the center of a filter over the reaction matrix of the device, using a transfer pipette. The specimen was allowed to soak through the matrix (approximately 10 seconds). Three drops of antibody-enzyme conjugate (alkaline phosphatase) were then added and the reaction matrix incubated for 60 seconds at room temperature.

The filter was next removed and discarded, and about 1 ml of a citrate/NaCl wash solution, combined with TWEEN and Triton buffer solutions, was added and allowed to flow through the matrix.

Three drops of a chromogenic enzyme substrate (Bromo-chloro indole phosphate nitro-blue tetrazolium) were then added, and the color allowed to develop in the matrix for a full two minutes. Thereafter, another 1.0 ml of the wash solution was added, and the results read visually. The appearance of a visually-detectable positive sign (+) indicated that the specimen contained elevated (greater than about 50 mIU/ml) levels of beta-hCG. Samples run using the foregoing procedure but not containing such elevated levels of beta-hCG produced a negative sign (−) in the matrix.

Tests run utilizing a substantially similar protocol to that of Example 8 but which did not result in the appearance of either a positive (+) or a negative (−) sign, indicated the improper addition of reagents, or indicated deterioration of reagents.

The following is a general example of the preparation of an analytical device according to the invention, which additionally incorporates a procedural control area for determining non-specific reactivity (interference) of the sample with the solid phase.

Reaction matrices utilizing the material of the invention can be prepared substantially as previously described, and the particles incorporated into the material in a pattern having substantially the overall shape of a "cross". The vertical axis of the "cross" can be formed of the particles having an analyte-binding substance upon their surfaces, whereas the horizontal axis of the "cross" can be formed of a substance capable of binding the enzyme label (i.e., antibody capable of becoming "conjugated" or attached to the label). Accordingly, when these reaction matrices are used in an assay (such as previously described), e.g., for beta-hCG, if no detectable level of analyte is present in the sample only the "procedural control area" of the matrix will produce a detectable response, i.e., the horizontal axis of the "cross" (a "minus" sign) will develop color or another response, indicating a negative result. However, if a detectable level of analyte is present, then the analyte will bind, along with the label, to the particles both in the horizontal and vertical axis, producing a detectable response in both axes (a "plus" sign).

Alternatively, the areas of the matrix in which the responses are produced can take the form of "dots", circles, numbers and the like. Thus, the microparticles can be sprayed or otherwise dispensed into the material of the matrix and incorporated therein, as previously described, in various patterns as desired. While the foregoing controls have been described in this Example as used in connection with the presently preferred matrix material of the invention, the on-board controls may be similarly employed in connection with other solid-phase analytical devices as previously described. The advantages of incorporation of such a procedural control into the material and device heretofore described, as well as into solid phase assay devices using other types of matrix materials, include a) a control provides a measure of validation of materials for each assay run; b) a control with each assay run enables comparative interpretation of results, especially when specific patterns, such as "plus" ("+") and "minus" ("−") signs are used; and c) the incorporation of a control into each assay device provides expedient validation of the assay, allowing the user to be more confident of the assay results.

It is to be appreciated that various modifications and changes can be made in the specific, preferred embodiments of the invention as described in detail herein, without departing from the spirit and scope of the invention, as set forth in the following claims.

What is claimed is:

1. A method for determining the presence or amount of an analyte in a fluid, comprising the steps of:
    a) incubating a sample of the fluid with a plurality of substantially spherical, solid particles having an average diameter of from about 0.1 to about 5 microns, the particles having immobilized upon their surfaces a binding substance which specifically binds the analyte, whereby the analyte becomes bound to the substance to form an analyte/binding substance complex on the particles;
    b) contacting a porous, fibrous matrix with the incubated particles, wherein the average diameter of said particles is less than the particle retention rating of said matrix and whereby at least a portion of the incubated particles become retained and immobilized within the matrix upon at least a portion of the fibers thereof;
    c) contacting said fibrous matrix containing the complex of the particles with a with a labeled substance capable of specifically binding the analyte, said labeled substance capable of producing a detectable response in the presence of the analyte and an indicator substance, whereby the labeled substance becomes bound to the complex on the particles;
    d) washing unbound labeled substance from said fibrous matrix;
    e) contacting said fibrous matrix with the indicator substance; and
    f) detecting the response produced as a function of the presence or amount of analyte in the sample.

2. The method of claim 1 wherein the labelled substance comprises an enzyme, the indicator substance comprises a chromogen, and detecting the response produced comprises detecting the presence or amount of chromogen in the fibrous matrix.

3. The method of claim 1 wherein the analyte is beta hCG.

4. The method of claim 1 wherein the analyte is a strep A antigen.

5. The method of claim 1 wherein the analyte is HBsAg.

6. A method of determining the presence or amount of an analyte in a test sample, comprising the steps of:
    a) contacting a porous matrix of fibers with the test sample wherein substantially spherical, solid particles having a substance adsorbed or bound to their surfaces which specifically binds the analyte, said coated particles having an average diameter between about 0.1 and about 5 microns and wherein the average diameter of said particles is less than the particle retention rating of the matrix are retained and immobilized upon the fibers of said matrix,
    b) contacting the porous fibrous matrix of step a) with a second substance which specifically binds the analyte and which is labeled with a substance capable of producing a detectable response in the presence of an indicator substance such that this second substance will bind to any analyte which has bound to the retained and immobilized particles, c) removing any second substance which has not bound to analyte bound to the retained and immobilized particles, d) contacting the porous matrix of step of step c with the indicator substance, and e) correlating any detectable response produced to the presence or amount of the analyte in the sample.

7. The method of claim 6, wherein the analyte is beta-hCG.

8. The method of claim 6, wherein the analyte is Strep-A antigen.

9. The method of claim 6, wherein the analyte is HBsAg.

10. The method of claim 6 wherein:

the detectable response resulting from the interaction of the second substance and the indicator substance is a visually detectable response, and prior to step a)

a second set of substantially spherical particles are retained and immobilized in the matrix, said second set of particles having a substance adsorbed or bound to their surfaces which specifically binds said second substance and having an average diameter between about 0.1 and about 5 microns and wherein the average diameter of said second particles is less than the particle retention rating of the matrix, the particles with an analyte binding substance adsorbed or bound to their surfaces and said second set of particles are arranged in a pattern such that after the matrix is contacted with the sample, the second substance and the indicator substance:

i) a visually detectable plus sign is displayed if detectable analyte is present in the sample as a result of indicator substance interacting with both second substance adhered to said second set of particles and second substance adhered to analyte adhered to said analyte binding particles and ii) a visually detectable minus sign is displayed if no detectable analyte is present in the sample as a result of indicator substance interacting with only the second substance adhered to the second set of particles.

11. A solid-phase assay device useful in a binding assay to determine the presence or an amount of an analyte in a fluid sample comprising a) a rigid carrier means for holding a porous matrix of fibers, b) a porous matrix of fibers arranged in a substantially planar layer having a first sample-contacting surface and a second surface opposed to said first surface, said matrix being disposed in said carrier means such that, when the device is used in the performance of an assay, at least a portion of the sample contacting the first surface passes through said substantially planar layer to the second surface, and c) substantially spherical, solid particles retained and immobilized on the fibers of said porous matrix, said particles having a substance adsorbed or bound to their surfaces which specifically binds analyte, said coated particles having an average diameter between about 0.1 and about 5 microns and wherein the average diameter of said particles is less than the particle retention rating of said porous matrix.

12. The solid phase assay device of claim 11, wherein the device additionally comprises filtering means disposed in relationship to the first surface of said substantially planar layer, such that, when the device is in use, sample fluid passes through said filtering means prior to contacting the first surface.

13. The solid phase assay device of claim 11, wherein the device additionally comprises absorbent means disposed in relationship to the second surface of said substantially planar layer, such that at least a portion of sample passing through said substantially planar layer is absorbed by said absorbent means.

14. The solid phase assay device of claim 13, wherein the device additionally comprises a barrier layer interposed between said substantially planar layer and said absorbent means, said barrier layer having one way permeability such that when the device is in use and a fluid is passed through said substantially planar layer, it restricts fluid retained by said absorbent means from returning to said substantially planar layer.

15. The solid phase assay device of claim 14, wherein the barrier layer is composed of a polyethylene weave material.

16. In a binding assay utilizing a solid-phase to determine the presence or amount of an analyte in a test sample comprising contacting the test sample with an immunoreactive porous matrix of fibers in order to capture the analyte and detecting the captured analyte, the improvement comprising capturing the analyte in a porous matrix of fibers in which substantially spherical, solid particles are retained and immobilized, said particles having a substance adsorbed or bound to their surfaces which specifically binds the analyte, said coated particles having an average diameter between about 0.1 and about 5 microns and wherein the average diameter of said particles is less than the particle retention rating of the porous matrix.

17. The binding assay of claim 16, wherein the binding assay is an enzyme immunoassay.

18. The binding assay of claim 16, wherein the binding assay is a competitive binding assay.

* * * * *